US008853191B2

(12) United States Patent
Wester et al.

(10) Patent No.: US 8,853,191 B2
(45) Date of Patent: *Oct. 7, 2014

(54) STANOL COMPOSITION AND THE USE THEREOF

(71) Applicant: Raisio Nutrition Ltd., Raisio (FI)

(72) Inventors: Ingmar Wester, Raisio (FI); Tapio Palmu, Raisio (FI); Tatu Miettinen, Espoo (FI); Helena Gylling, Helsinki (FI)

(73) Assignee: Raisio Nutrition Ltd., Raisio (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/718,637

(22) Filed: Dec. 18, 2012

(65) Prior Publication Data

US 2013/0237506 A1  Sep. 12, 2013

Related U.S. Application Data

(63) Continuation of application No. 12/731,907, filed on Mar. 25, 2010, now Pat. No. 8,349,821, which is a continuation of application No. 11/819,379, filed on Jun. 27, 2007, now abandoned, which is a continuation of application No. 11/070,208, filed on Mar. 3, 2005, now abandoned, which is a continuation of application No. 10/223,633, filed on Aug. 20, 2002, now abandoned, which is a continuation of application No. 09/051,080, filed as application No. PCT/FI96/00465 on Sep. 2, 1996, now abandoned.

(30) Foreign Application Priority Data

Aug. 9, 1996  (FI) .......................................... 963126

(51) Int. Cl.
A61K 31/56  (2006.01)
A61K 31/575  (2006.01)
A23D 7/01  (2006.01)
A23L 1/30  (2006.01)

(52) U.S. Cl.
CPC .............. *A61K 31/575* (2013.01); *A23D 7/013* (2013.01); *A23L 1/3004* (2013.01)
USPC ........................................................ 514/170

(58) Field of Classification Search
CPC .............................. A61K 31/56; A61K 31/575
USPC ........................................................ 514/170
See application file for complete search history.

(56) References Cited

U.S. PATENT DOCUMENTS

| | | | |
|---|---|---|---|
| 2,704,764 A | 2/1952 | Mattikow et al. | |
| 2,729,655 A | 1/1956 | Miller et al. | |
| 3,335,154 A | 8/1967 | Smith et al. | |
| 3,751,569 A | 8/1973 | Erickson et al. | |
| 3,881,005 A | 4/1975 | Thakkar et al. | |
| 4,195,084 A | 3/1980 | Ong | |
| 5,244,887 A | 9/1993 | Straub | |
| 5,270,041 A | 12/1993 | Eugster et al. | |
| 5,502,045 A | 3/1996 | Miettinen et al. | |
| 5,965,449 A * | 10/1999 | Novak .............................. 436/71 |

FOREIGN PATENT DOCUMENTS

| | | |
|---|---|---|
| DE | 22 48 921 | 11/1974 |
| EP | 0 911 385 A1 | 4/1999 |
| WO | 98/06405 | 2/1998 |

OTHER PUBLICATIONS

"Sitosterol," The Penguin Dictionary of Chemistry, D.W. A. Sharp, Ed., 2nd Ed., p. 361 (1990).
Armstrong, MR, Cary MC., Thermodynamic and molecular determinants of sterol solubilities in bile salt micelles. J. Lipid Res 1987; 28: 1144-1155.
Augustine, R, Reardon, Jr. EJ 1969. The palladium catalyzed hydrogenation of cholesterol. Org Prep and Proced 1969; 1: 107-109.
Becker, M, Staab D, Von Bergmann K. Treatment of severe familial hypercholesternia in childhood with sitosterol and sitostanol, J. Pediatr 1993; 122:292-296.
Comparison of the effects of plant sterol ester and plant stanol ester-enriched margarines in lowering serum cholesterol concentrations in hypercholesterolaemic subjects on a low-fat diet, Hallikainen et al., Eur. J. of Clin. Nutr. (2000) 54: 715-725.
Czubayko F, Beumers B, Lammsfuss S, Lutjohann D, von Bergmann K. A simplified micromethod for quantification of fecal excretion of neutral and acidic sterols for outpatient studies in humans, J Lipid Res 1991; 32: 1861-1867.
Dayal B, Tnt GS, Batta AK, Speck J, Khachadurian AK, Shefer S, Salen G., Identification of 5-☐ tanols in patients with sitosterolemia and xanthomatosis: stereochemistry of the protonolysis of steroidal organoboranes. Steroids 1982; 40:233-243.
Declaration by Ilkka Etupaltta, Jan. 18, 2001.
Dieter Lütjohann et al., "Sterol absorption and sterol balance in phytosterolemia evaluated by deuterium-labeled sterols: effect of sitostanol treatment," J. Lipid Research 36:1763-1773 (1995).
Dutta PC, Appelqvist LA. Saturated sterols (stanols) in unhydrogenated and hydrogenated vegetable oils and in cereal lipids. J. Sci Food Agric 1996; 71: 383-391.
Effects of Low-Fat Yogurt with Plant Stanol Esters and of Consumption Frequency on LDL-Cholesterol Levels, J. Plat et al., Summary of Presentation at 92nd AOCS Annual Meeting and Expo, May 13-16, 2001, Minneapolis, Minnesota, USA.
Efficacy of spreads enriched with stanol-stearate esters on blood cholesterol levels, Annex I filed with the Opponent's further submissions of Jun. 27, 2000.
Elintarvike-tekniikan Perusteet, M.Hiros et al., VAPK-kustannus, Helsinki, 1990, pp. 236-241, and translation of passage bridging pp. 240-241.

(Continued)

Primary Examiner — Gollamudi Kishore
(74) Attorney, Agent, or Firm — Arent Fox LLP

(57) ABSTRACT

A stanol composition containing in addition to sitostanol as the main component, also a substantial amount of at least 10% campestanol has been found to effectively lower serum cholesterol levels when incorporated in edible commodities. Upon esterification the composition is especially useful in edible fats and oils and in fat-containing foods.

12 Claims, No Drawings

(56) References Cited

OTHER PUBLICATIONS

English Translation of Miettinen, Duodecim 112, No. 13, 1996, pp. 1149-1154.

Fate of Dietary Sterols in Hydrogenated Oils and Fats, P.W. Parodi, J.Am. Oil Chem. Soc., vol. 52:345-348, 1975.

Formation of Sitostanol During Partial and Full Hydrogenation of Vegetable Soybean Oil with Ni-Catalyst, Raisio Benecol Ltd's hydrogenation results, filed with the EPO in the opposition of EP corresponding to WO 92/19640 on Jul. 19, 2001.

Fred H. Mattson et al., "Effect of Plant Sterol Esters on the Absorption of Dietary Cholesterol," Journal of Nutrition 107:.1139-1146 (1977).

Fred H. Mattson et al., "Effect of Plant Sterol Esters on the Absorption of Dietary Cholesterol," The Procter & Gamble Company, Miami Valley Laboratories, pp. 1139-1146, 1977.

Front page of WO 92/19640, published Nov. 12, 1992.

Grungy, SO, Mo HCI. Effects of low dose phytosterols on cholesterol absorption in man. In: Greten H. (Ed.). Lipoprotein metabolism. SpringerVerlag, Berlin, Heidelberg, New York, 1976: 112-118.

Gylling, H, Miettinen TA, Serum cholesterol lowering by dietary sitostanol is associated with reduced absorption and synthesis of cholesterol and decreased transport of LDL apoprotein B in men with type 11 diabetes. In: Gotto Jr. AM, Mancini M., Richter WO, Schwandt P (Eds.) Treatment of severe dyslipoproteinemia in the prevention of coronary heart disease, 4th Int.Symp Munich 1992 Karner.

Gylling, H., et al., "Serum cholesterol and cholesterol and lipoprotein metabolism in hypercholesterolemic NIDDM patients before and during sitostanol ester-margarine treatment," Diabetologia, 1994, vol. 37, pp. 773-780.

Gylling, H., Miettinen TA. Serum cholesterol and cholesterol and lipoprotein metabolism in hypercholesterolemic NIDDM patients before and during sitostanol ester-margerine treatment. Diabetologia 1994, 37: 773-780.

Gylling, H., Simes MA, Miettinen TA. Sitastanol ester margarine in dietary treatment of children with familial hypercholesterolemia. J. Lipid Res. 1995; 36: 1807-1912.

Hassan, AS, Rampone, AJ. Intestinal absorption and lymphatic transport of cholesterol and 11-sitostanol in the rat. J. Lipid Res 1979; 20: 646-653.

Heinemann, T, Axtmann G, von Bergmann K. Comparison of intestinal absorption of cholesterol with different plant sterols in man. Eur J Clin Invest 1993; 23: 827-831.

Heinemann, T, Kullack-Ublick GA Pietruck B, Von Bergmann K. Mechanisms of action of plant sterols on inhibition of cholesterol absorption. Eur J Clin Pharmacol 1991; 40:59-63.

Heinemann, T, Leiss O, von Bergmann, K. Effect of low-dose sitostanol on serum cholesterol in patients with hypercholesterolemia. Atherosclerosis 1986; 61: 219-223.

Heinemann, T, Pietruck B, Kullack-Ublick G, von Bergmann K. Comparison of sitosterol and sitostanol on inhibition of intestinal cholesterol absorption. Agents Actions (Suppl) 1988; 26: 117-122.

Hydrogenation of sterol esters. Demonstration of hydrogenation of sterol moiety, Annex II filed with the Opponent's further submission of Jun. 27, 2000.

Ikeda I, Kawasaki A, Samezima K, Sugano M. Antihypercholesterolemic activity of □-sitostanol in rabbits. J Nutri Sci Vitaminol 1981; 27: 243-251.

Ikeda I, Sugano M. Comparison of absorption and metabolism of □-sitosterol and □162-sitostanol in rats. Atheroscierosis 1978; 30: 227-237.

Ikeda I, Tanabe Y, Sugano M. Effects of sitosterol and sitostanol on micellar solubility of cholesterol. J Nutr Sci Vitaminol 1989; 35: 361-369.

Jandacek RJ, Webb MR, Mattson FH. Effect of an aqueous phase on the solubility of cholesterol in an oil phase. J. Lipid Res 1977; 18:203-210.

Kaukas Woodbased Chemicals. Product Description for Kaukas Ultra Sitosterol. Feb. 1986.

Lees AM, Mok HYI, Lees RS, McCluskey MA, Grundy SM. Plant sterols as cholesterol lowering agents: clinical trials in patients with hypercholesterolemia and studies of sterol balance. Atherosclerosis 1977; 28: 325-338.

Lees RS, Lees AM. Effects of sitosterol therapy on plasma lipid and lipoprotein concentrations. In: Greten H. (Ed.) Lipoprotein metabolism. Springer-Verlager, Berlin, Heidelberg, New York, 1976: 119-124.

Ling WH, Jones PJH. Minireview dietary Phytosterols: A review of metabolism, benefits and side effects. Life Sciences 1995; 57: 195-206.

Lutjohann, Dieter et al., "Sterol absorption and sterol balance in phytosterolemia evaluated by deuterium-labeled sterols: effect of sitostanol treatment," Journal of Lipid Research, vol. 36, 1995, pp. 1763-1773.

Mattson, FH, Grundy SM, Crouse JR. Optimizing the effect of plant sterols and cholesterol absorption in man. Am J Clin Nutr 1982; 35:697-700.

Mattson, Fred H. et al., "Optimizing the effect of plant sterols on cholesterol absorption in man1-3," The American Journal of Clinical Nutrition 35, Apr. 1982, pp. 697-700 and 2 pages of drawings.

Method for Qualitative and Quantitative Determination of Phytosterols in Vegetable lots by LC-GC off-line, Schuhmann et al., Mitt. Gebiete Lebensm. Hyg., vol. 87:708-715, 1996.

Miettinen, Duodemic 112, No. 13, 1996, pp. 1149-1154.

Miettinen, TA, Koivisto P. Non-cholesterol sterols and bile acid production in hypercholesterolaernic patients with ileal bypass. In: Paurngarter G, Stiehl A, Gerok W (Eds.). Bile Acid and Concentration in Health and Disease. IVITP Press, Boston 1983: 183-187.

Miettinen, TA, Puska P, Gylling H, Vanhanen H, Vartiainen E. Reduction of serum cholesterol with sitostanol-ester margarine in a mildly hypercholesterolemic population. New Eng J Med 1995; 333: 1308-1312.

Miettinen, TA, Vanhanen H. Dietary sitostanol related to absorption, synthesis and serum level of cholesterol in different alipoprotein E phenotypes. Aterosclerosis 1994; 105: 217-226.

Nestel, P., et al., "Cholesterol-lowering effects of plant sterol esters and non-esterified stanols in margarine, butter and low-fat foods," European Journal of Clinical Nutrition, 2001, vol. 55, pp. 1084-1090.

O.J. Pollak and David Kritchevsky, "Sitosterol", Monographs on Atherosclerosis, VIII + 220, pp. 84-87, ISBN 3-8055-0568-X, 1981.

Page 2 of the International Preliminary Examination Report of WO 92/19640, dated Aug. 4, 1993.

Page 2 of the Written Opinion of WO 92/19640, dated Apr. 14, 1993.

PCT Applicant's Guide (Swedish Patent Office as IPEA) (Jul. 1998).

PCT Applicant's Guide (Swedish Patent Office as ISA) (Jul. 1999).

Pollak OJ. Effect of plant sterols on serum lipids and atherosclerosis. Pharmac Ther 1985; 31: 177-208.

Richard M. Carroll et al., "Lipids and Lipoproteins," The Clinical Chemistry of Laboratory Animals, Walter F. Loeb and Fred W. Quimby, Eds., pp. 106-107 (1989).

Salen G, Ahrens Jr. EH, Grundy SM. Metabolism of □-sitosterol in man. J Clin Invest 1970, 49:952-967. J Nutri Sci Vitaminol 1981; 27: 243-251.

Saturated Sterols (Stanols) in Unhydrogenated and Hydrogenated Edible Vegetable Oils and in Cereal Lipids, Dutta et al., J. Sci. Food Agric., vol. 71:383-391, 1996.

Serum Plant Sterols and Cholesterol Precursors Reflect Cholesterol Absorption and Synthesis in Volunteers of a Randomly Selected Male Population, Miettinen et al., Am. J. Epiderm., vol. 131, No. 1:20-31, 1990.

Stanol Components in Edible Fats and Oils, M. Sugano et al., Sci. Byull. Fac. Agr. Kyushu Univ., vol. 32, No. 1:21-28, 1977.

Sugano, M, Kamo F, Ikeda I, Morioka H. Lipid-lowering activity of phytostanols in rats. Atherosclerosis 1976; 24:301-309.

Sugano, M., Morioka H, Ikeda I. A comparison of hypocholesterolemic activity of □-sitosterol and □-sitostanol in rats. J Nutr 1977; 107: 2011-2019.

The Penguin Dictionary of Chemistry, Second Edition, 1990, pages: cover, copyright, and 361.

TS. Milkova et al., "Sterol Composition of Bulgarian Soya and Corn Oils," Die Nahrung 21(1):7-12 (1977).

(56) References Cited

OTHER PUBLICATIONS

Vanhanen HT, Blomquist S, Enholm C, Hyvenen M, Jauhiainen M, Torstila I, Miettinen TA. Serum cholesterol, cholesterol precursors, and plant sterols in hypercholesterolemic subjects with different apoE phenotypes, during dietary sitostanol ester treatment. J Lipid Res 1993; 34: 1535-1544.

Vanhanen HT, Kajander J, Lehtovirta H, Miettinen TA. Serum levels, absorption efficiency, faecal elimination and synthesis of cholesterol during increasing doses of dietary sitostanol esters in hypercholesterolaemic subjects. Clin Sci 1994; 87: 61-67.

Vanhanen HT, Miettinen TA. Effects of unsaturated and saturated dietary plant sterols on their serum contents. Clin Chim Acta 1992; 206: 97-107.

* cited by examiner

STANOL COMPOSITION AND THE USE THEREOF

FIELD OF THE INVENTION

The present invention relates to a sitostanol containing composition of plant stanols especially for use as a serum cholesterol level lowering substance. The invention also relates to the corresponding esterified form of such a composition which advantagously can be used in edible oils and fats and in fat-containing foods.

BACKGROUND OF THE INVENTION

Plant sterols are essential components of all plants. Their functions in plants resemble the functions of cholesterol in mammals. The most abundant plant sterols in the flora are β-sitosterol, campesterol and stigmasterol. The chemical structure of these plant sterols is very similar to that of cholesterol the differences occurring in the side chain of the backbone of the molecule. For example, compared to cholesterol, the side chain of sitosterol contains an additional ethyl group and the side chain of campesterol an additional methyl group.

Since 1950's plant sterols have been known to effectively reduce the serum cholesterol levels. Even when administered in relatively small doses (a few grams a day) they reduce the absorbability of both biliary and dietary cholesterol effectively and thus lower the serum total and LDL-cholesterol levels (12, 28, see also 27, 32). The mechanism by which the restriction of cholesterol absorption happens is still not known in, detail, but it is assumed that plant sterols displace cholesterol from the micellar phase and thereby prevent its absorption. In practically all of the early studies, sitosterol or its hydrogenated form sitostanol has been the main plant sterol of interest. However, the sterol composition of the tested preparations has not always been well documented, and the sterol preparations used in most studies have also contained different amounts of other sterols.

Plant sterols have been considered as a safe way of lowering serum cholesterol levels, since they are natural components of vegetable fats and oils. Additionally, their absorption from the intestine of healthy subjects is limited, and the limited amounts absorbed are excreted from the body in the bile. The absorbtion rate of the plant sterols varies between individuals and between the different plant sterols, but for healthy humans usually less than 5% of the plant sterols are absorbed from the digestive tract (27). However, up to 10% of dietary campesterol has been shown to be absorbed (20).

In few rare diseases such as sitosterolemia plant sterols are absorbed exceptionally efficiently, and also the elimination from the body via the biliary route is impaired. Serum levels of sitosterol, campesterol and also their saturated forms sitostanol and campestanol are highly elevated. The elevated levels of the saturated stanols are most probably due to their more effective endogenous synthesis rather than a more effective absorption (10, 27). If untreated, sitosterolemia leads already at young age to xanthomatosis and coronary heart disease. For people with this disease, an administration of unsaturated plant sterols in amounts greater than normally present in foods may lead to hazardous health effects.

Lees and Lees (25) tested the effects of three different sitosterol preparations on plasma lipid and lipoprotein concentrations. One of the preparations was Cytellin, a commercial preparation (Eli Lilly Co., USA) that contained 60-65% sitosterol and 35-40% other sterols, mainly campesterol. An average dose of 18 g/day divided in three doses resulted in a 10.5% average fall in plasma total cholesterol and a 15% fall in LDL-cholesterol. However, when only traces of plant sterols including campesterol are normally detected in plasma (10, 33), the plasma concentration of campesterols varied from 4 to 21 mg/dl in the subjects tested by Lees and Lees (25). In the discussion the authors stated very strongly that since the atherogenicity of campesterol is unknown, the use of a sitosterol preparation with a relatively high campesterol content like the Cytellin preparation used in their study cannot be recommended.

Further, Lees et al. (26) studied the efficacy of plant sterols from soybean oil and tall oil in lowering the blood cholesterol level. They used two different physical forms of each plant sterol, namely a suspension and a powder. The soy sterol consisted of 60-65% sitosterol and 35% campesterol, and a daily dose of an average 18 g of sterols per day (range 9-24 g) was given in three equal doses. A tall oil sterol preparation with only about 5% campesterol was used in this study. A daily dose of 3 grams of both tall oil sterol preparations (powder and suspension) was tested. Additionally, a dose of 6 grams of the tall oil sterol suspension was tested.

Soy sterol in both physical forms and tall oil sterol in powder form reduced the plasma cholesterol content by on average 12% (26). However, the relatively high absorbability of campesterol that has already been shown earlier, was observed also in this study. In the 5 patients tested the plasma campesterol levels ranged from 5 to 21 mg/dl (mean 16 mg/dl). Thus again, even if the cholesterol-lowering effect of soy sterol was proved to be significant, the authors did not recommend its use as a cholesterol lowering agent. On the contrary, they recommended that pharmaceutical plant sterol preparations should contain a minimum of campesterol and a maximum of sitosterol. Based on the two studies cited above, it can be concluded that the use of vegetable oil based sterols such as soy sterol are strongly not recommendable.

Saturated plant sterols such as sitostanol and campestanol are present in most vegetable oils only in trace amounts. However, tall oil sterols contain 10-15% of sitostanol, the saturated form of sitosterol. Sitostanol can also be made by hydrogenation of the double bond in sitosterol. In the-latest studies made with both experimental animals and humans, sitostanol has been proven to be more effective as a cholesterol-lowering agent than sitosterol (8, 16, 17, 18, 19, 36).

An additional advantage of sitostanol is that it is virtually unabsorbable. Several studies (e.g. 9, 16, 17, 21) have shown that sitostanol is practically unabsorbable while small amounts (<5%) of its unsaturated form sitosterol (33) can be absorbed. Similarily, in an in vitro study Amstrong and Carey (6) also showed that cholestanol, a saturated form of cholesterol, was more hydrophobic and less absorbable than cholesterol.

When sitostanol is made by hydrogenation of the most usual plant sterol sources, also another saturated plant sterol, namely campestanol, is formed from campesterol. Until recently, relatively little has been known about the absorbability and the possible hypocholesterolemic effect of this stanol. Based on the data cited above stating that saturated sterols are less absorbable than their unsaturated forms, it could be hypothesized that campestanol might be virtually unabsorbable.

To study the absorbability of different plant sterols Heinemann et al. (20) compared the intestinal absorption of cholesterol with campesterol, sitosterol, stigmasterol and also low concentrations of sitostanol and campestanol in humans by means of intestinal perfusion technique. The results showed that the absorption rate of the differed plant sterols varied between different plant sterols being on average 4.2% for sitosterol, 4.8% for stigmasterol, 9.6% for campesterol and 12.5% for campestanol. Large variation between the absorption efficacy in the ten male subjects was detected.

Thus, according to Heinemann et al. (20) campestanol was found to be more efficiently absorbed than its unsaturated form campesterol. This is against the assumption based on studies cited earlier that showed that the saturated sterols (sitostanol, cholestanol) would be less absorbable than the unsaturated ones (sitosterol, cholesterol). The reason for this remains unclarified. Heinemann et al. (20) speculated, though, that the reason for this conflicting result might be that the study of Amstrong and Carey (6) was made with in vitro conditions and that the theory of the hydrophobicity being a major factor in micellar binding and/or absorption might not be relevant in in vivo conditions. However, this speculation does not explain the fact that several studies that have shown the poorer absorbability of sitostanol compared to that of sitosterol have been made under in vivo conditions. Thus the results of Heinemann et al. (20) that conflict with previous results remained unexplained by the authors.

Sugano et al. (34) studied the hypocholesterolemic activity of corn sterols (composition: 31% campesterol, 4% stigmasterol and 65% sitosterol) and corn stanols (composition: 31% campestanol and 69% sitostanol) obtained by hydrogenation of a corn oil sterol mixture. Two experiments were carried out in rats. Both the sterol and the stanol showed hypocholesterolemic effects at the level of 0.5-1% of the diet when cholesterol (1% in the diet) was ingested. In the first experiment no significant difference was seen in the hypocholesterolemic effect of phytosterols and phytostanols. However, in the second experiment, at the same dietary levels the phytostanols showed considerably greater ability to lower the plasma cholesterol concentration than did the phytosterols (statistically significant at $p<0.02$). Moreover, rats fed the 1.0% stanol diet had plasma cholesterol levels significantly lower ($p<0.02$) than that of the animals fed the diet free of cholesterol. This was not observed in rats fed the 1.0% sterol diet.

Sugano et al. (34) did not study the difference in hypocholesterolemic effect between stanol mixtures with a high content of sitostanol and a low content of campestanol (tall oil sterol based) and stanol mixtures with a substantially higher level of campestanol (vegetable oil sterol based). They compared the hypocholesterolemic effect of an unsaturated sterol mixture with the corresponding saturated stand mixture. Later studies made by this research group have been focused on the cholesterol lowering effect of sitostanol spedifically and Compared to sitosterol (21, 22, 23, 35). In fact, in a later publication (23) they refer to the phytostanol study mentioned above (34) mentioning only the hypocholesterolemic effect of β-sitostanol compared to 13-sitosterol without discussing any hypocholesterolemic effect of saturated sterols (including campestanol) compared to unsaturated sterols. In the later studies mentioned aboVe sterol mixtures with the typical composition of hydrogenated tall oil sterols with a high content of sitostanol (>90%) have been used.

Miettinen and Vahhanen (30) have shown that sitostanol in fatty acid ester form is more effective than free sitostanol in lowering serum cholesterol levels. Later studies have also shown that the use of sitostanol esters as a part of a daily diet is an effective way of reducing serum total and LOL-cholesterol concentrations (13, 14, 15, 31, 37, 38). The benefit of using stenol esters instead of free stenol is also that the stanol esters are fat-soluble and can therefore easily be incorporated into a wide variety of foods without changing the taste, flavor or physical behavior of the final product. The method for the preparation of sitostanol fatty acid esters and the use of fat-soluble stenol esters in foods have been disclosed in U.S. Pat. No. 5,502,045 (2), hereby incorporated by reference.

Straub (3) suggests the use of saturated stanols (sitostanol, clionastanol, 22,23-dihydrobrassicastanof, campestanol and mixtures thereof) in a method for making a food additive composition where stanols are mixed with an edible solubility agent, an effective amount of a suitable antioxidant and an effective amount of a suitable dispersant. These food additives are intended to reduce cholesterol absorption from foods and beverages which contain cholesterol, e.g. meat, eggs and dairy products. However, in this patent no data showing either any clinical effects or the absorbtion of dietary sterols is presented.

Eugster et al. (1) teach the use of small amounts of sterols, their fatty acid esters and glucosides for the treatment of tumors. The methods of preparation proposed by Eugster et al. involve hazardous chemical reagents like N,N'-carbonyl diimidazole, thionyl chloride and solvents like tetrahydrofuran, benzen, chloroform or dimethylformamide. Eugster et al. comment on the possible use of these substances as dietary foods and as food additives, but do not present any data on hypocholesterolemic effects or make any claims covering such use. From the disclosure of Eugster et al. it is hard to get a clear picture of how the end product is purified to yield a pure enough sterol ester in large amounts enough to be used as a food component. The only purifying processes referred to are thin layer chromatography and high performance liquid chromatography. This being the case, the preparation method referred to in the patent by Eugster et al. is limited to small amounts only.

The U.S. Pat. No. 3,751,569 (4) discloses the addition of plant sterol fatty acid esters to cooking oil with the objective of lowering the serum cholesterol levels in man. The patent proposes, for use in the esterification of free sterols, a method which in no case fulfills the requirement for preparation of a food-grade product. According to the patent, the esterification is carried out between a free sterol and a fatty acid anhydride, with perchloric acid acting as a catalyst. The catalyst and reagent used cannot be accepted in food processes. In addition, the patent relates to the fatty acid esters of only native plant sterols. The method proposed in the German patent DE 22 48 921 (5) for the esterification of sterols present in oils and fats by a chemical interesterification technique fulfils the criteria of food processes. In this patent, free sterol and an excess of fatty acid esters are added to a mixture of oil or fat, whereafter the entire fat blend is interesterified by a commonly known interesterification technique. In the resulting fat blend virtually all free sterols have been converted to fatty acid esters. The purpose of this is to protect free sterols in vegetable and animal oils against possible changes during processing.

Earlier data shows that campesterol, one of the major plant sterols, is absorbed relatively efficiently. Therefore it has been recommended that only plant sterol mixtures with a minimum content of campesterol should be used. This has in practice lead to the use of sterol mixtures such as tall oil sterols with a high content of sitosterol.

Most work on stanols has covered sitostanol only. The study of Heinemann et al. (20) showing that campestanol, the saturated form of campesterol, is more readily absorbed than campesterol or sitosterol (12.5%, 9.6% and 4.2% respectively) has lead to a "consensus" that saturated sterol mixtures with "elevated" levels of campestanol are unsafe due to the absorption of campestanol. A clear evidence of this is that all clinical studies covering the use of stanols (sitostanol) have been based on sterol mixtures with a high level of sitostanol and a low level of campestanol.

It is an established fact from many studies (e.g. 8, 17, 18, 19, 23, 36), that sitostanol, the saturated form of sitosterol, is more effective than the corresponding unsaturated sitosterol in reducing the blood cholesterol level. Furthermore saturated sterols are absorbed in very, limited amounts, which make the use of saturated sterols a safe mean of reducing cholesterol on a population bases. Of the unsaturated sterols especially campesterol is absorbed in amounts high enough to call for strong recommendations against the use of sterol mixtures with eleveted levels of campesterol (eg. vegetable oil based sterol mixtures) (25, 26).

Accordingly there has been a strong prejudice against using campestanol in any substantial amounts as a substance to be added to foods and this has seriously limited the spectrum of phytosterol containing raw materials to such containing a relatively minor amount of campesterol and its saturated form, campestanol.

BRIEF DESCRIPTION OF THE INVENTION

This invention relates to plant stanol compositions containing sitostanol as a main component but with substantial amounts of campestanol, either in free form or esterified as fatty acid esters for lowering the level of blood serum cholesterol.

The invention further relates to the use of stanol compositions containing sitostanol as the main component but also substantial amounts of campestanol, or fatty acid esters thereof in edible commodities as a dietary component for lowering blood serum cholesterol levels.

The object of the present invention is to broaden the spectrum of plant raw materials useful in the preparation of substances for edible commodities, especially edible oils and fats and fat-containing foods intended to control cholesterol levels in blood serum. The invention enables using as raw materials for these purposes plant oils and fats containing in addition to sitosterol also a substantial amount of campesterol.

Suitable raw materials for use in the preparation of the compositions of the present invention are e.g. corn, soybean and rapeseed but also other plants with a phytosterol composition high in campesterol may be used.

The novel composition of the present invention, and especially its esterified form, may be incorporated in food substances such as cooking oils, margarines, butter, mayonnaise, salad dressings, shortenings, cheeses (including unripened and ripened cheeses) and other fat-containing foods.

The composition of the present invention can also be consumed as such.

DETAILED DESCRIPTION OF THE INVENTION

According to the present invention, the plant stenol composition contains, in 15 addition to its main component, sitostanol, also a substantial amount of at least 10% campestanol.

The compostion preferably contains as much as from 20% to 40% and most preferably: from 25% to 35%, e.g. about 30% campestanol or its fatty acid ester when the composition has been esterified to make it lipophilic.

Throughout this specification all percentages are given by weight, unless otherwise specified. In this specification the bracketed numbers refer to publications listed in the appended List of References.

Data obtained surprisingly and against prevailing prejudice shows that a hydrogenated stanol mixture containing sitostanol as the main component but with substantial amounts of campestanol is at least as effective as a stanol mixture containing over 90% sitostanol and a low level of campestanol, indicating that campestanol is at least as effective in reducing the absorption of cholesterol as sitostanol. Moreover, data from sterol analysis of blood serum clearly shows that campestanol remains virtually unabsorbed, with blood serum contents being about 40% smaller than that of sitostanol. Thus a stenol mixture containing sito-stenol as a major component but with substantial amounts of campestanol must be regarded as at least as safe as a conventional tall sterol based stanol mixture. This data is in striking contrast to current opinion regarding the efficacy and safety of stanol mixtures with elevated amounts of campestanol (see 20, 27, 34).

The U.S. Pat. No. 5,502,045 (2) showed that fatty acid esters of sitostanol are more effective in reducing the blood cholesterol level than the free sitostanol. Later studies have clearly confirmed the cholesterol lowering effect of a margarine containing fat soluble sitostanol fatty acid esters (e.g. 31).

The use of stanol fatty acid esters instead of free stanols is crucial for abroad use of these in various fat containing food products because only the stanol fatty acid esters are soluble in edible oils and fats in amounts high enough to reach levels effective in reducing the absorption of both dietary and biliary cholesterol from the digestive tract.

The solubility of stanol esters in edible oils and fats is as high as 35-40%; whereas the solubility of free sterols in edible oils and fats is limited to a maximum of 2 percent by weight only at the temperature of 21° C. (24). Higher amounts could be incorporated by using different surfactancts, solubilizing or dispersing agents, but even the use of these substances does not ensure fat solubility. The use of the above substances is usually restricted or even prohibited by law. Furthermore free sterols at a level of 1% will affect the physical properties of the fat or, oil, causing changes in the structure and physical behaviour of the product. This is not the case when stanol fatty acid esters are used since the physical: properties of the fat mixture can easily be modified by altering the fatty acid composition of the mixture.

It is obvious that stanol fatty acid esters easily can be incorporated to other foods than margarines and spreads as described in this invention. The U.S. Pat. No. 5,502,045 (2) gives further examples of possible use. It is, however, obvious to those skilled in the art that stanol fatty acid esters can be added to a wide variety of foods, especially fat-containing foods.

Many methods for preparing fatty acid esters of sterols have been proposed. The drawbacks of these methods are that almost all of them use reagents, which cannot be accepted in the production of a product intended to be used as a macronutrient in foods. The use of toxic reagents like thionyl chloride or anhydride derivatives of fatty acids is common.

The preferred method of preparing stenol fatty acid esters of sterols is described in the U.S. Pat. No. 5,502,045 (2, hereby incorporated by reference). This procedure is based on the interesterification process used widely by the edible fat and oil industry. This esterification process deviates advantageously from previous methods in that no other substances than the free stenol, a fatty acid ester or a fatty acid ester mixture and a interesterification catalyst like sodium ethylate are used. One important feature of the method is that one of the reactants, the fatty acid ester is used in excess and functions as a solvent, solubilizing the stanol under the conditions used (vacuum 5-15 mmHg). The reaction gives a mixture of fatty acid esters and stanol fatty acid esters. The stanol fatty acid ester can easily be concentrated into almost pure stanol fatty acid esters by vacuum destillation, which removes the excess of fatty acid esters. Alternatively the blend can be added as such to the final fat blend before the deodorizing step is carried out.

Stanols are found in small amounts in nature eg. in wheat, rye, corn and tritricale and can thus be found in small amounts (11, 14) in the daily food. Stanols can easily be produced by hydrogenation of natural sterol mixtures. Only tall sterol mixtures with high enough purity (sterol content >98%) to be used as such for food use were commercially available in early 1996. Plant sterols with substantial amounts of campesterol such as vegetable oil based sterol mixtures can e.g. be obtained as a by-product of tocopherol production from vegetable oil distillates. The obtained plant sterols can be converted into stanols by prior known hydrogenation techniques such as that based on the use of Pd/C catalyst in organic solvents (7, hereby incorporated by reference). It is obvious for those skilled in the art that a wide variety of Pd catalysts and solvents can be used to carry out the hydrogenation, which when done under optimized conditions leaves only small amounts of unsaturated sterols unconverted while the formation of the typical dehydroxylated by-products stanes and stenes remains at a low level (<1.5%).

The instant invention compares the hypocholestelolemic effect of a stanol mixture containing a high level of sitostanol that is generally regarded by experts in the field to be the safest and most effective plant sterol in reducing cholesterol absorption and thereby serum cholesterol levels with a stanol mixture containing a substantial amount of campestanol. In this specification, for the first time, hypo-cholesterolemic effects of vegetable oil based stanols in humans have been reported. This invention is the first to show that a stanol mixture with a substantial amount of campestanol (over 10% and preferably about 30%) is at least as effective as stanol mixtures with high levels of sitostanol. Furthermore, the results of the present study clearly indicate that campestanol on the contrary to what has been reported by Heinemann et al. (20) is virtually unabsorbed.

Clinical Studies

To study the hypocholesterolernic effects of vegetable oil stanol ester and tall oil stanol ester margarines a 5-week double blind cross over study with a 2 weeks wash-out period was designed. The test arrangement of the study was as follows:

Test Arrangement of the Intervention Study.

Numbers 1-6 indicate the blood samples collected at the home diet (1, 2), after the first intervention period (3, 4) and after the second intervention period (5, 6). VS=vegetable oil based stanol ester margarine, TS=tall oil based stanol ester margarine.

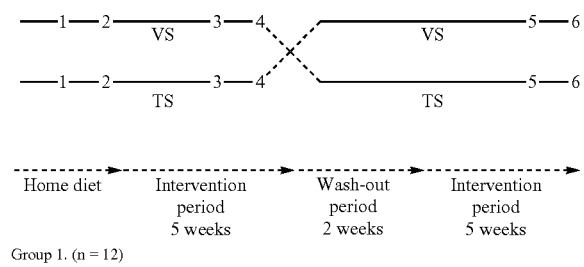

Group 1. (n = 12)
Group 2. (n = 12)

Twenty-four voluntary, free-living, healthy women with a moderately elevated cholesterol level (average 6.12±0.16 mmol/l) consumed about 25 g per day (a 250 g tub/10 days) of the test margarines as a part of the daily diet in a random order. Serum lipids (total cholesterol, LM-cholesterol, HEX-cholesterol and tri-glycerides) and serum sterol contents were measured at the home diet and at the end of each test period: Blood samples were taken twice, one week apart at the home diet and by the end of each test margarine perios. The obtained serum lipid values are shown in Table 1 below.

TABLE 1

Serum lipid concentrations (mmol/l, mean ± SE) during the home diet and after the five-week treatment with vegetable oil stanol ester margarine (VS) and tall oil stanol ester margarine (TS), (n = 24).

|  | Home diet | VS | TS |
|---|---|---|---|
| Total cholesterol | 6.12 ± 0.16 | 5.77 ± 0.18* | 5.95 ± 0.23 |
| LDL-cholesterol | 4.03 ± 0.15 | 3.60 ± 0.17* | 3.76 ± 0.19* |
| HDL-cholesterol | 1.54 ± 0.09 | 1.62 ± 0.09* | 1.63 ± 0.10* |
| Triglycerides | 1.22 ± 0.13 | 1.20 ± 0.11 | 1.26 ± 0.15 |

*p < 0.05 or less

Both test margarines resulted in favourable changes in serum lipids. The reduction in LDL-cholesterol values and the increase in HDL-cholesterol values were statistically significant (p<0.05 or less). Furthermore, the vegetable oil based sterol ester resulted also in a statistically significant reduction of total cholesterol. The obtained reduction of total cholesterol and LDL-cholesterol was higher with the vegetable oil based stanol ester margarine compared to the tall oil based stand ester margarine. No changes in triglyceride levels were obtained. The serum lipid results obtained indicate that a vegetable oil stanol ester margarine containing a substantial amount of campestanol in its stanol fraction might be even more effective than the tall oil stanol ester margarine. Tall oil stanol ester margarine has in earlier studies (14, 15, 31) shown effective hypocholesterolemic effects. Thus, based on the cross-over design of this study, it can be concluded that vegetable oil based stanols are showing at least as effective hypocholesterolemic effects as tall oil based stanols.

Serum sterol concentrations were quantified with gas-liquid cromatography according to a previously published method (29, hereby incorporated by reference). The means of two measurements of serum lipids from the blood samples taken at each period were calculated. The data on mean serum plant sterol concentrations at the home diet and after each test period and the mean changes observed in these concentrations are presented in Tables 2 and 3 below.

TABLE 2

Serum plant sterol concentrations (mean ± SE, Ng/dl) during the home diet and after each intervention period (n = 24). Vegetable oil based stanol ester margarine, TS = tall oil based stenol ester margarine.

|  | Home diet | VS | TS |
|---|---|---|---|
| Campestanol | 47 ± 2 | 58 − 3. | 47 ± 3 |
| Sitostanol | 94 ± 3 | 92 ± 5 | 96 ± 5 |
| Campesterol | 472 ± 37 | 337 ± 25 | 350 ± 28 |
| Sitosterol | 277 ± 17 | 198 ± 12 | 227 ± 15 |

*p < 0.05 or less

TABLE 3

Mean changes (±SE) in the serum plant sterol concentrations (pg/dl),
(n = 24). VS = Vegetable oil based stanol ester margarine, TS = tall oil
based stanol ester margarine, HD = home diet.

|  | Δ (VS − HD) | Δ (TS − HD) | Δ (VS − TS) |
|---|---|---|---|
| Campestanol | 11 ± 2* | 0 ± 2 | 11 ± 2* |
| Sitostanol | −2 ± 3 | 2 ± 4 | −4 ± 4 |
| Campesterol | −134 ± 19* | −122 ± 91* | −12 ± 13 |
| Sitosterol | −80 ± 11* | −51 ± 12* | −29 ± 8* |

*p < 0.05 or less

Both test margarines significantly lowered serum campesterol and serum sitosterol levels. The serum concentration of campesterol is known to reflect intestinal cholesterol absorption in humans (29, 39). Thus, the lower the campesterol value, the lower the percentage of intestinal cholesterol is absorbed.

Marked falls in serum campesterol levels (25-28%) during the study periods indicates that both stanol ester margarines decreased the intestinal absorption of cholesterol. Furthermore, no differences in the serum sitostanol concentration could be seen while mean serum campestanol concentration after the vegetable oil stanol ester period was significantly higher than at the home diet and after the tall oil stanol ester period. However, the absolute concentration of campestanol was only about 63% of that of sitostanol, which is generally regarded as virtually unabsorbable. This low serum concentration of campestanol clearly indicates that the absorption of campestanol is very limited, which is in conflict with the results presented by Heinemann et al. (20). Thus, since stanol mixtures containing high levels of sitostanol are regarded as safe for human ingestion, stenol mixtures containing substantial amounts of campestanol must be regarded as equally safe based on the fact that campestanol is like sitostanol virtually unabsorbable.

The preparation of the stand ester composition of the invention and the margarines used in the above clinical studies are disclosed in detail in the following working examples:

EXAMPLE 1

Hydrogenation of Sterol Mixtures

A commercially available sterol mixture obtained from vegetable oil distillate (composition: brassicasterol 2.7%, campesterol 26.7%, stigmasterol sitosterol 49.1% and sitostanol 2.9%) was hydrogenated in a pilot scale reactor (25 l). 26 g of a fibrous Pd catalyst (Smop-20; Pd content 10 weight-%, Smoptech, Turku, Finland), 26 g distilled water for the activation of the catalyst and 11.7 kg propanol was feed into the reactor. The reactor was flushed with nitrogen and the activation of the catalyst was carried out under hydrogen gas at a pressure of 1 bar and at a temperature of 65° C. for 30 min. After the activation the blend was cooled to 40° C., after which 1.3 kg of the sterol blend was added.

The propanol sterol mixture was heated under nitrogen atmosphere to 65° C., after which nitrogen was displaced by hydrogen. After that a thorough flushing with hydrogen was done, the hydrogenation reaction was carried out at a hydrogen pressure of 1 bar. The normal conversion time is about 120 min. The conversion can easily be monitored by taking aliquots, which are analyzed by HPLC.

The hydrogen pressure was dropped and the reactor was flushed with nitrogen. The fibrous catalyst was filtered off with nitrogen pressure. The propanol stanol blend was left to crystallize overnight at 10° C. after which the stanol crystals were vacuum filtered and the cake was washed with 0.5 kg cold propanol. The obtained stanol mixture was dried at 60° C. in a vacuum cupboard. The yield was 75% and the composition of the obtained stenol mixture was as follows according to capillary GC analysis: campesterol 0.2%, campestanol 28.9%, stigmasterol 0.1%, sitosterol 0.2%, sitostanol 70.1%. It should be noted that brassicasterol is hydrogenated into 24β-methyl cholestanol, an epimer of campestanol, but since these appear in the same peak with ordinary capillary gas chromatographic procedures which is unable to separate according to chirality, it is usually calculated as campestanol. Based on the initial sterol mixture the content of 24β-methyl cholestanol should be 2.7%.

EXAMPLE 2

Preparation of Stanol Fatty Acid Esters

A stanol fatty acid ester mixture was prepared on a pilot scale. 6 kg stanols obtained by combining several batches obtained by the hydrogenating procedure given in example 1 was dried overnight at 60° C. and esterified with a 8.6 kg low erucic acid rapeseed oil methyl ester mixture: The sterol composition of the stand blends used was as follows: Campesterol 0.4%, campestanol (+24β-methyl cholestanol) 29.7%, stigmasterol 0.1%, sitosterol 0.4% and sitostanol 68.0%. The stanol content of the blend was 98.2%. The esterification was carried out as follows:

A mixture of stanols and low erucic rapeseed oil fatty acid methyl ester was heated in a reactor vessel at 90-120° C. under a vacuum of 5-15 mmHg. After drying for 1 hour, 21 g Na-ethylate was added and the reaction was continued for about 2 hours. The catalyst was destroyed by the addition of 30% water (by weight) at 90° C. After phase separation the water phase was removed and a second washing was carried out. After the separation of the water phase, the oily phase was vacuum dried at 95° C. with a stirring effect of 200 rpm. The stanol fatty acid mixture was lightly bleached for 20 min. at 30 mmHg and a temperature of 110° C. with 1.0% of bleaching earth (Tonsil Optimum FF, S0dchemie, Germany) under a stirring effect of 200 rpm. The bleaching earth was filtered off and the obtained mixture of fatty acid methyl esters and stanol fatty acid esters can be added as such to fat blends prior to deodorization or the excess of methyl esters can be distilled off under vacuum. Accordingly the blend can be deodorized to obtain a tasteless stanol fatty add ester mixture, which can be added as such to different food manufacturing processes.

EXAMPLE 3

Production of Margarines for the Clinical Studies

80% margarines with tall oil stanol fatty acid esters and vegetable oil based stanol fatty esters were produced on a Gerstenberg & Agger 3×57 pilot scale perfector. Tall oil stanol fatty acid esters were obtained from the normal production of Benecol® margarine by Raision Margariini, Finland. A normal trans fatty acid free fat blend (composition: 30% non-hydrogenated interesterified vegetable fat and 70% liquid LEAR oil) to which the stanol fatty acid mixtures were added was used: The stanol content of the final product was targeted to be 12 g/100 g product, which would provide a daily intake of 3 g stanols at usage level of 25 g/day. The products were produced according to following recipe:

| | |
|---|---|
| Fat blend including the stanol fatty acid esters | 80% |
| Water | 19% |
| Salt | 0.5% |
| Emulsifier, Dimodan BP | |
| Na-bidarbonate and citric acid as pH-regulating agents | |
| B-carotene as colouring agent | |
| Flavours. | |

The obtained margarines were packed into 250 g polypropene tubs, which were sealed by an aluminium foil. The taste and texture of the products were equal to commercial margarines.

The stenol content of the tall oil stenol margarine was 12.7 g/100 g product and of the vegetable oil based stanol margarine 12.6 g/100 g product. The sterol composition of the two products were as follows:

| | Tall oil based stanol margarine | Vegetable oil based stanol margarine |
|---|---|---|
| Brassicasterol | 0.3% | 0.4% |
| Campesterol | 2.2% | 2.4% |
| Campestanol | 7.5% | 27.6% |
| Sitosterol | 7.4% | 4.2% |
| Sitostanol | 82.5% | 63.8% |
| Others | 0.1% | 1.6% |

LIST OF REFERENCES

US Patent Specification
Ref. Nr.
1 Eugster C, Eugster C, Haldemann W, Rivara G. Sterols, their fatty acid esters and glocosides; processes for their preparation; spontaneously dispersible agents containing these compounds, and their use for treatment of tumors. 1993. U.S. Pat. No. 5,270,041.
2 Miettinen T A, Vanhanen H, Wester I. Use of stanol fatty acid ester for reducing serum cholesterol level. 1996. U.S. Pat. No. 5,502,045.
3 Straub C D. Stanois to reduce cholesterol absorption from foods and methods of preparation and, use thereof. 1993. U.S. Pat. No. 5,244,887.
4 Clear cooking and salad oils having hypocholesterolemic properties. 1973. U.S. Pat. No. 3,751,569.
Other Patent Specification
5 Baltes J, Merkle R. Verfahren zur Herstellung eines Gemisches aus pflanzlichen und tierischen Olen bzw. Felten and Fettsauresternestern. German patent DE 22 48 921.
Other Publications
6 Amstrong M J, Carey M C. Thermodynamic and molecular determinants of sterol solubilities in bile salt micelles. J Lipid Res 1987; 28: 1144-1155.
7 Augustine R L, Reardon Jr. E J 1969. The palladium catalyzed hydrogenation of cholesterol. Org Prep and Proced 1969; 1: 107-109.
8 Becker M, Staab D, Von Bergmann K Treatment of severe familial hypercholesterolemia in childhood with sitosterol and sitostanol. J pediatr 1993; 122: 292-296.
9 Czubayko F, Beumers B, Lammsfuss S, Lutjohann D, von Bergmann K. A simplified micro-method for quantification of fecal excretion of neutral and acidic sterols for outpatient studies in humans. J Lipid Res 1991; 32: 1861-1867.
10 Dayal B, Tnt G S, Batta A K, Speck J, Khachadurian A K, Shefer S, Salen G. Identification of 5-a stanols in patients with sitosterolemia andxanthomatosis: stereochemistry of the protonolysis of steroidal organoboranes. Steroids 1982; 40: 233-243.
11 Dutta P C, Appelqvist L A. Saturated sterols (stands) in unhydrogenadted and hydrogenated edible vegetable oils and in cereal lipids. J Sci Food Agric 1996; 71: 383-391.
12 Grundy S M, Mok H Y I. Effects of low dose phytosterols on cholesterol absorption in man. In: Greten H (Ed.) Lipoprotein metabolism. Springer-Verlag, Berlin, Heidelberg, N.Y., 1976: 112-118.
13 Gylling H, Miettinen T A, Serum cholesterol lowering by dietary sitostanol is associated with reduced absorption and synthesis of cholesterol and decreased transport of LDL apoprotein B in men with type II diabetes. In: Gotto Jr A M, Mancini M, Richter W O, Schwandt P (Eds.) Treatment of severe dyslipoproteinemia in the prevention of coronary heart disease. 4th Int Symp Munich 1992, Karger, Basel, 1993: 57-59.
14 Gylling H, Miettinen T A. Serum cholesterol and cholesterol and lipoprotein metabolism, in hypercholesterolemic NIDDM patients before and during sitostanol ester-margarine treatment. Diabetologia 1994; 37: 773-780.
15 Gylling H, Slimes M A, Miettinen T A. Sitostanol ester margarine in dietary theatment of children with familial hypercholesterolemia. J Lipid Res 1995; 36: 1807-1912.
16 Hassan A S, Rampone A J. Intestinal absorption and lymphatic transport of cholesterol and p-sitostanol in the rat. J Lipid Res 1979; 20: 646-653.
17 Heinemann T, Leiss O, von Bergmann K. Effect of low-dose sitostanol on serum cholesterol in patients with hypercholesterolemia. Atherosclerosis 1986; 61: 219-223.
17 Heinemann T, Pietruck B, Kullack-Ublick G, von Bergmann K. Comparison of sitosterol and sitostanol on inhibition of intestinal cholesterol absorption. Agents Actions (Suppl) 1988; 26: 117-122.
18 Heinemann T, Kullak-Ublick G-A, Pietruck B, von Bergmann K. Mechanisms of action of plant sterols on inhibition of cholesterol absorption. Eur J Clin Pharmacol 1991; 40: 59-63.
20. Heinemann T, Axtmann G, von Bergmann. K Comparison of intestinal absorption of cholesterol with different plant sterols in man. Eur J Clin Invest 1993; 23: 827-831.
21 Ikeda I, Sugano M. Comparison of absorption and metabolism of sitosterol and p-sitostanol in rats. Atherosclerosis 1978; 30: 227-237.
22 Ikeda I, Tanabe Y, Sugano M. EffectS of sitosterol and sitostanol on micellar solubility of cholesterol. J Nutr Sci Vitarriinol 1989; 35: 361.-369.
23 Ikeda I, Kawasaki A, Samezima K, Sugano M. Antihyper cholesterolemic activity of (3-sitostanol in rabbits. J Nutr Sci Vitaminol 1981; 27: 243-251.
24 Jandacek R J, Webb M R, Mattson F H. Effect of an aqueous phase on the solubility of cholesterol in an oil phase. J Lipid Res 197.7; 18: 203-210.
25 Lees R S, Lees A M. Effects of sitosterol therapy on plasma lipid and lipoprotein concentrations. In: Greten H (Ed.) Lipoprotein metabolism. Springer-Verlag, Berlin, Heidelberg, N.Y., 1976: 119-124.
26 Lees A M, Mok H Y I, Lees R S, McCluskey M A, Grundy S M. Plant sterols as cholesterol-lowering agents: clinical trials in patients with hyper-cholesterolemia and studies of sterol balance. Atherosclerosis 1977; 28: 325-338.
27 Ling W H, Jones P J H. Minireview dietary phytosterols: A review of metabolism, benefits and side effects. Life Sciences 1995; 57: 195-206.

28 Mattson F H, Grundy S M, Crouse J R. Optimizing the effect of plant sterols on cholesterol absorption in man. Am J Clin Nutr 1982; 35: 697-700.
29 Miettinen T A, Koivisto P. Non-cholesterol sterols and bile acid production in hypercholesterolaemic patients with Heal bypass. In: Paumgarter G, Stiehl A, Gerok W Eds.). Bile acid and concentration in health and disease. MTP Press, Boston 1983: 183-187.
30 Miettinen T A, Vanhanen H. Dietary sitostanol related to absorption, synthesis and serum level of cholesterol in different apolipoprotein E phenotypes. Aterosclerosis 1994; 105: 217-226.
31 Miettinen. T A, Puska P, Gylling H, Vanhanen H, Vartiainen E. Reduction of serum cholesterol with sitostanol-ester margarine in a mildly hypercholesterolemic population. New Engl J Med 1995; 333: 1308-1312.
32 Pollak O J. Effect of plant sterols on serum lipids and atherosclerosis. Pharmac Ther 1985; 31: 177-208.
33 Salen G, Ahrens Jr. E H, Grundy S M. Metabolism of 13-sitosterol in man. J Clin Invest 1970, 49: 952-967. J Nut Sci. Vitaminol 1981; 27:243-251.
34 Sugano M, Kamo F, Ikeda I, Morioka H. Lipid-lowering activity of phytostanols in rats. Atherosclerosis 1976; 24: 301-309.
35 Sugano M, Morioka H, Ikeda I. A comparison of hypocholesterolemic activity of 13-sitosterol and 13-sitostanol in rats. J Nutr 1977; 107: 2011-2019.
36 Vanhanen H T, Miettinen T A. Effects of unsaturated and saturated dietary plant sterols on their serum contents. Clin Chim Acta 1992; 205: 97-107.
37 Vanhanen H T, Blomqvist S, Enholm C, HyvOnen M, Jauhiainen M, Torstila I, Miettinen T A. Serum cholesterol, cholesterol precursors, and plant sterols in hypercholesterolemic subjects with different apoE phenotypes during dietary sitostanol ester-treatment. J Lipid Res 1993; 34: 1535-1544.
38 Vanhanen H T, Kajander J, Lehtovirta H, Miettinen T A. Serum levels, absorption efficiency, faecal elimination and synthesis of cholesterol during increasing doses of dietary sitostanol esters in hyper-cholesterolaemic subjects. Clin Sci 1994; 87: 61-67.
39 Tilvis R S, Miettinen T A. Serum plant sterols and their relation to cholesterol absorption. Am J Clin Nutr 1986; 43: 92-97.

The invention claimed is:

1. A method of lowering the blood serum campesterol level in a human subject, comprising administering to the subject an effective amount of a composition comprising a plant stanol composition, wherein
the stanols are present in free form, or as a mixture of fatty acid esters and stanols in free form,
the stanol part of the stanol composition comprises sitostanol and campestanol, and
the campestanol is present in an amount of 20 to 40 weight-% of the stanol part.

2. The method of claim 1, wherein campestanol is present in an amount of 25 to 35 weight-% of the stanol part.

3. The method of claim 1, wherein campestanol is present in an amount of about 30 weight-% of the stanol part.

4. The method of claim 1, wherein the stanol part is derived from plant sterols.

5. The method of claim 4, wherein the stanol part is derived from vegetable oil sterols.

6. The method of claim 5, wherein the stanol part is derived from corn, soybean or rapeseed sterols.

7. The method of claim 1, wherein the plant stanol composition is administered at a daily dose of about 3 grams per day.

8. The method of claim 1, wherein the stanol part is synthetically produced.

9. The method of claim 1, wherein the plant stanol composition is administered orally.

10. The method of claim 1, wherein the plant stanol composition is administered as a component of a food composition.

11. The method of claim 10, wherein the food composition is selected from the group consisting of cooking oil, margarine, butter, mayonnaise, salad dressing, shortening, cheese and other fat-containing food.

12. The method of claim 1, wherein the method further lowers serum total or LDL-cholesterol levels.

* * * * *